United States Patent [19]
Howard et al.

[11] Patent Number: 5,968,544
[45] Date of Patent: Oct. 19, 1999

[54] COMPOSITIONS CONTAINING CREATINE

[75] Inventors: Alan Norman Howard, Great Shelford; Roger Charles Harris, Newmarket, both of United Kingdom

[73] Assignee: The Howard Foundation, Cambridge, United Kingdom

[21] Appl. No.: 08/866,517

[22] Filed: May 30, 1997

[30]    Foreign Application Priority Data

May 31, 1996 [GB] United Kingdom ............... 9611356

[51] Int. Cl.[6] .................................................. A61K 9/14
[52] U.S. Cl. ........................ 424/439; 424/489; 426/69
[58] Field of Search ........................... 424/489, 439; 426/69

[56]           References Cited

U.S. PATENT DOCUMENTS

| | | | |
|---|---|---|---|
| 3,615,600 | 10/1971 | Tonsbeek | 99/140 N |
| 4,464,409 | 8/1984 | De Rooij | 426/536 |
| 4,647,453 | 3/1987 | Meisner | 424/54 |
| 4,772,591 | 9/1988 | Meisner | 514/62 |

FOREIGN PATENT DOCUMENTS

| | | |
|---|---|---|
| 0 669 083 | 8/1995 | European Pat. Off. . |
| 59-025663 | 2/1984 | Japan . |
| 950087771 | 9/1996 | Japan . |
| 94/02127 | 2/1994 | WIPO . |
| 96/15488 | 7/1994 | WIPO . |
| 94/17794 | 8/1994 | WIPO . |
| 96/04240 | 2/1996 | WIPO . |
| 96/14063 | 5/1996 | WIPO . |
| 96/36348 | 11/1996 | WIPO . |

*Primary Examiner*—Thurman K. Page
*Assistant Examiner*—James M. Spear
*Attorney, Agent, or Firm*—Lee, Mann, Smith, McWilliams, Sweeney & Ohlson

[57]           ABSTRACT

Disclosed is an acidic composition for human consumption, comprising creatine. In particular the composition is conveniently an isotonic drink for storage at 4° C., or is a dry stable powder which may be stored at ambient temperature.

21 Claims, 6 Drawing Sheets

Fig. 6 though not when in solution. The dry powder composition is reconstituted into the acidic liquid or semi-liquid composition when the user mixes the powder with water immediately prior to consumption.

COMPOSITIONS CONTAINING CREATINE

FIELD OF THE INVENTION

This invention relates to compositions for human consumption comprising creatine and to a method of providing stable creatine-containing compositions.

BACKGROUND OF THE INVENTION

Governments are currently concerned with the high incidence of obesity (and lesser degrees of weight gain) in populations, since they represent a known risk-factor for coronary heart disease, hypertension and diabetes. Besides dietary modification, the main thrust of treatment and weight maintenance after weight loss is physical exercise. It is now suggested by experts that diet alone is insufficient in the long term in maintaining weight loss without altering lifestyle, in particular the taking of more exercise. However one of the problems overweight people experience is that they find physical activity tiring and are easily fatigued. There is a need for a regime which will make obese people less fatigued so that they can exercise for longer periods, burn up more calories and lose more weight, or maintain their weight better after weight loss.

Moreover, in the last few years there has been considerable interest among athletes in creatine, which occurs abundantly in skeletal muscle. Creatine plays a pivotal role in the regulation and homeostasis of skeletal muscle energy metabolism and it is now generally accepted that the maintenance of phospho-creatine availability is important to the continuation of muscle force production. Although creatine synthesis occurs in the liver, kidney and pancreas it has been known for sometime that the oral ingestion of creatine will add to the whole body creatine pool, and it has been shown that the ingestion of 20 to 30 g creatine per day for several days can lead to a greater than 20% increase in human skeletal muscle total creatine content. Thus WO94/02127 discloses the administration of creatine in amounts of at least 15 g (or 0.2–0.4 g/kg body weight) per day, for at least 2 days, for increasing muscular strength.

In fact, it was subsequently found that after several days of supplementation (20 g per day) with creatine it takes no more than 2 to 3 g per day to maintain the saturation of body stores. Creatine supplementation in an appropriate dose can provide improvements to athletes involved in explosive events, which include all events lasting from a few seconds to a few minutes (such as sprinting, swimming, weight-lifting etc.). Endurance performance in events lasting longer than about 30 minutes appears to be unaffected by creatine supplementation. Creatine is a normal food component and is not a drug and its use is not contrary to official regulations. The biggest benefits of supplementation can be experienced by vegetarians or those who eat no meat or fish since these people tend to have low muscular creatine content.

Over the last few years there has been considerable interest in the use of isotonic drinks for people indulging in physical exercise. Human body fluids comprise water and substances dissolved therein, such as mineral salts known as electrolytes. These enable electrical impulses to stimulate muscle action. Isotonic drinks replace essential electrolytes lost in sweat during and/or after exercise. The term isotonic is applied to drinks containing the same concentration of minerals as in body fluids and in which the osmotic pressure is the same as that exerted by human body fluids. The most important electrolytes used in isotonic drinks are sodium, chloride, potassium, calcium, magnesium and phosphorus. Isotonic drinks can be made already diluted with water or conveniently packaged in sachets or cans as a powder which can then be mixed with still or carbonated water to give a refreshing flavoured drink of, for instance, a citrus flavour.

It is well known that creatine is unstable in aqueous solutions at acid or neutral pH, and is converted into the related compound creatinine. This is highly significant as creatinine has no muscle performance-enhancing effect and is excreted from the human body as a waste product in urine. In view of the foregoing, EP 0 669 083 teaches that aqueous drinks for human consumption comprising creatine must be weakly alkaline, in order to prevent the conversion of creatine into creatinine, and this has become the generally accepted opinion.

SUMMARY OF THE INVENTION

In a first aspect the invention provides an acidic composition for human consumption, comprising creatine. The term acidic is intended to mean that the composition, in aqueous form, has a pH below 7.0. Thus, where the composition is a liquid or semi-liquid, it has an acidic pH, and where the composition is a dry powder it is such that when mixed with water (at substantially neutral pH) it gives rise to an acidic liquid. In particular the composition desirably has a pH between 2.5 and 6.5, preferably between 3.0 and 6.0. Typically the composition has a pH in the range 3.5–5.5 which, to the human palate, has a refreshingly sharp taste without being too acidic.

The creatine content of the composition may be present as any active form of creatine, (e.g. creatine phosphate) but creatine monohydrate is found particularly convenient as a form of creatine.

The composition may be in the form of a dry powder or may be provided in liquid or semi-liquid form (e.g. as a drink or yogurt, respectively). In preferred embodiments the composition is a drink which is isotonic (i.e. corresponds to the osmotic potential of human body fluids) and/or comprises electrolytes. Desirably the composition will both comprise electrolytes and be isotonic. When provided as a liquid, the composition will conveniently be packaged in conventional consumer packages, such as bottles, cans, foil pouches and the like.

The present inventors have found that the conversion of creatine to creatinine at acidic pH is actually sufficiently slow as to allow physiologically useful amounts of creatine to remain in the composition after considerable periods of time, such that creatine may be presented in acidic formulations, contrary to the teaching of the art. In particular, the conversion of creatine to creatinine can be greatly inhibited by storage (e.g. in commercial chiller cabinets at 4–8° C.) of the composition at lower than ambient temperatures.

Thus, in a second aspect the invention provides a method of storing an acidic liquid or semi-liquid composition comprising creatine, for human consumption, the method comprising storage of the composition below ambient temperature, typically in a commercial chiller cabinet at 4–8° C. of the conventional sort familiar from any medium or large-sized food retailer. Typically the composition is an aqueous drink (preferably isotonic) or a yogurt or similar semi-liquid foodstuff. The drink may be still or carbonated, and preferably comprises a citrus flavouring.

Alternatively the composition may be provided as a dry powder which, upon mixing with (preferably dissolution in) a pre-determined volume of liquid (e.g. of substantially neutral pH) gives rise to an acidic solution. The creatine content of the composition is stable in the dry powder form at ambient temperature. Appropriate doses of the powder can then be used, as required, to make up fresh drinks with the creatine content substantially undiminished. The powder may be mixed with or dissolved in any suitable liquid (e.g. water, milk) or semi-liquid (e.g. yogurt). When provided as a powder, the composition may conveniently be packaged in conventional consumer packages (preferably hermetically sealed) such as foil sachets or pouches, tubes, tubs and the like.

Accordingly in a further aspect the invention provides a method of supplying a creatine-containing composition for human consumption, the method comprising providing a creatine-containing acidic composition as a dry, stable powder which, when mixed with water or a suitable aqueous solution gives an acidic drink comprising creatine. Desirably the drink will comprise physiologically effective quantities of creatine (i.e. of the order of 3 grams or so, which is found in the prior art to be sufficient to maintain maximum levels of creatine in a human subject once saturation has been attained).

Typically the powder is such that, when a certain amount is dissolved in a pre-determined volume of water, it provides an isotonic drink. Desirably, the powder is provided as unitary doses (of about 10–20 grams) which may be dissolved in 200–350 mls of water to provide an isotonic drink. The unitary doses are conveniently supplied individually packaged in sachets, bags, packets, cylinders, bottles or other suitable packaging means. Preferably the package is hermetically sealed (e.g. a thin foil sachet) to prevent the ingress of water or water vapour. In some embodiments it may be desired to provide with the package a volumetric measuring means to allow a user to measure out an appropriate volume of water in which to dissolve the contents of the package. Typically this may take the form of a water-tight container (e.g. of plastics material) with one or more graduations to indicate a certain volume. The container may take the form of a beaker or similar vessel, to hold water in which the composition may be dissolved, and from which the resulting solution may be drunk.

The composition will preferably comprise one or more further components to improve its palatability, stability, flavour or nutritive quality. These further components may include electrolytes, as already mentioned above, or may be selected from the group consisting of: vitamins, lipids, carbohydrates, amino acids, trace elements, colourings, flavours, artificial sweeteners, anti-oxidants, stabilisers, preservatives, and buffers.

People on slimming diets often receive a reduced intake of vitamins, so these may be included with advantage in the composition of the invention. The following vitamins may be added in amounts which range from 20 to 100% of their recommended daily allowance (RDA). The following are typical of those which are useful: vitamin E, vitamin C, thiamin, riboflavin, niacin, vitamin B6, folacin, vitamin B12, biotin, and pantothenic acid.

In some cases a lipid component may be desirable. The carbohydrate content (if any) of the composition may be present as starch (particularly soluble starch) and/or sugars. The carbohydrates employed in the invention should preferably be used in quantities which are consistent with the isotonicity of the composition in its preferred embodiments, taking into account the effect of creatine content. The drink's osmolality should preferably not exceed 320 mOsm + or −10%. The sugars which may be present in the composition include glucose, fructose, sucrose, and maltose.

Artificial sweeteners which can be used include Aspartame, Acesulfam K, Saccharin and Cyclamate. Almost any desired flavouring can be added, most preferably citric flavours such as lemon, orange and grapefruit. Citric acid may also be used as an acidulant and as a buffering agent.

Colouring can be provided, typically by using a cold water soluble colourant such as beta carotene. Other suitable colourings will be apparent to those skilled in the art.

A clouding agent may be included in the composition to improve the appearance of the finished drink and distinguish it from lemonade.

The minerals can be added in any type or form which gives in combination the correct osmolarity and/or contains electrolytes in amounts which approximate the composition of the body fluids. It is convenient to provide the calcium and potassium in the form of their phosphates or hydrogen phosphates, and magnesium as the oxide or carbonate. Typically the amounts are: sodium at 400 mg/liter, calcium at 100 mg/liter, chloride at 600 mg/liter, potassium at 200 mg/liter, magnesium at 75 mg/liter and phosphorus at 50 mg/liter.

The amount of creatine per liter of prepared drink may range from 0.5 to 30 g, with a preferred content of about 12 g per liter. The normal serving size is in the range 250–330 ml, providing about 3 g or creatine. During the first 4 days of creatine supplementation the recommended consumption is 1.5 liters per day divided in 4 to 5 parts per day to achieve creatine saturation. This is followed by 1 drink of 250 ml per day containing 3 g of creatine to provide a maintenance level of creatine.

In some embodiments, the composition may additionally comprise pyruvate and/or dihydroxyacetone. Pyruvate and dihydroxyacetone are ergogenic compounds present in the body and have been shown to enhance submaximal endurance (R. T. Stanko et al., 1993 Sports Sciences 11, 17–23) and when substituted for part of the carbohydrate in the diet are useful in increasing weight loss in low energy diets (R. T. Stanko et al., 1992, Am. J. Clin. Nutr. 56, 630–5).

Pyruvate may be provided as a salt, preferably the sodium, potassium, magnesium or calcium salt. Pyruvate may be used without dihydroxyacetone, or as a mixture therewith, for example as a 1:3 (P:DHA) mixture. The total amount of pyruvate and/or DHA per 250 ml serving of the composition may be in the range 1 to 25 g, conveniently 5–15 g.

The invention will now be further described by way of illustrative example and with reference to the accompanying drawings, in which:

EXAMPLES

Example 1

This example describes the detailed formulation of an acidic composition in accordance with the invention. The composition takes the form of a dry powder, which is to be dissolved in water to constitute an isotonic drink comprising creatine.

| Ingredients | |
| --- | --- |
| Dextrose Monohydrate | 300 g |
| Citric Acid | 32 g |
| Pectin (stabiliser) | 6.0 g |
| Salt | 5.0 g |
| Trisodium Citrate | 5.0 g |
| Beta carotene | 3.0 g |
| Potassium Chloride | 2.9 g |
| Grapefruit Flavour | 2.9 g |
| Tricalcium Phosphate | 2.1 g |
| Heavy Magnesium Carbonate | 2.1 g |
| Vitamin Premix | 1.8 g |
| Lemon Flavour | 1.4 g |
| Orange Flavour | 1.4 g |
| Aspartame | 1.0 g |
| Creatine monohydrate | 88 g |

63 g of the above mixture when dissolved in 1 liter of water provides, per 250 ml serving, about 3 g creatine, energy kg 203 (kcal 48), 11.1 g carbohydrate, 156 mg chloride, 100 mg sodium, 52 mg potassium, 26 mg calcium, 19.5 mg magnesium, 13 mg phosphorus, vitamins (Vitamin E 3.4 mg, Vitamin C 16.2 mg, Thiamin 0.3 mg, Riboflavin 0.4 mg, Niacin 5.0 mg, Vitamin B6 0.4 mg, Folacin 85 µg, Vitamin B12 0.9 µg, Biotin 0.08 mg and Pantothenic acid 2.2 mg) and traces of protein, fat, and fibre. This provides a refreshing isotonic drink containing electrolytes and creatine which is relatively lower in calories than conventional isotonic drinks, and has a pH of about 3.8.

Example 2

This example relates to another embodiment of the invention. The formulation is as in example 1 above, except that the 300 g dextrose monohydrate is omitted and the aspartame content is increased to 2.5 g to compensate. When 5.3 g of this formulation is dissolved in 250 ml water, it provides an almost calorie free drink containing creatine and electrolytes which, whilst not isotonic, is nutritionally useful to those wishing to lose or maintain their weight.

Example 3

This example relates to another embodiment of the invention. The formulation is as in example 1 above, except that half of the dextrose monohydrate is omitted and replaced by the same weight of sodium, calcium or potassium pyruvate, together with the addition of 0.75 g of aspartame (giving a total amount of 1.75 gms aspartame). A typical serving of this formulation is 15.75 g mixed in 250 ml water.

Example 4

This example relates to a study of the stability of creatine in sterile conditions at acid pH over a period of two weeks.

A dry powdered composition in accordance with the invention was prepared and stored in 14 gram samples. The composition was essentially that described in example 1. Each 14 gm sample of the composition comprised about 3 gms of creatine. 14 grams of the powdered composition were dissolved in 400 ml of distilled water, and the solution incubated under sterile conditions at 25–26° C. for 2 weeks. The pH of the composition at the start of the experiment was 3.66.

5 ml aliquots of the solution were drawn aseptically over the course of the experiment and analysed for creatine and creatinine concentration. These determinations were made simultaneously be reversed-phase ion-pairing high-performance liquid chromatography, according to the method of Murakita (1988 J. of Chromatography 432, 471–473). The experiment was performed in triplicate and the results shown below in Table 1.

TABLE 1

| | 0h | 1h | 2h | 3h | 4h | 6h | 8h | 1d | 2d | 3d | 4d | 1w | 2w |
| --- | --- | --- | --- | --- | --- | --- | --- | --- | --- | --- | --- | --- | --- |
| Cr mmol/l | 53.0 | 53.1 | 53.1 | 54.7 | 53.2 | 51.7 | 52.1 | 48.1 | 49.6 | 46.1 | 42.5 | 38.8 | 31.7 |
| (±SD) | 1.3 | 0.0 | 1.5 | 0.9 | 2.1 | 0.1 | 0.8 | 2.1 | 1.0 | 0.5 | 0.8 | 1.4 | 0.1 |
| Cr g/400 ml | 2.78 | 2.79 | 2.79 | 2.87 | 2.79 | 2.71 | 2.73 | 2.52 | 2.60 | 2.42 | 2.23 | 2.04 | 1.66 |
| (±SD) | 0.07 | 0.00 | 0.08 | 0.05 | 0.11 | 0.01 | 0.04 | 0.11 | 0.05 | 0.03 | 0.04 | 0.07 | 0.01 |
| % Cr remaining | 100 | 100 | 100 | 99.3 | 99.3 | 99.3 | 99.0 | 96.2 | 91.7 | 87.6 | 84.3 | 74.7 | 57.5 |

Figure 1:
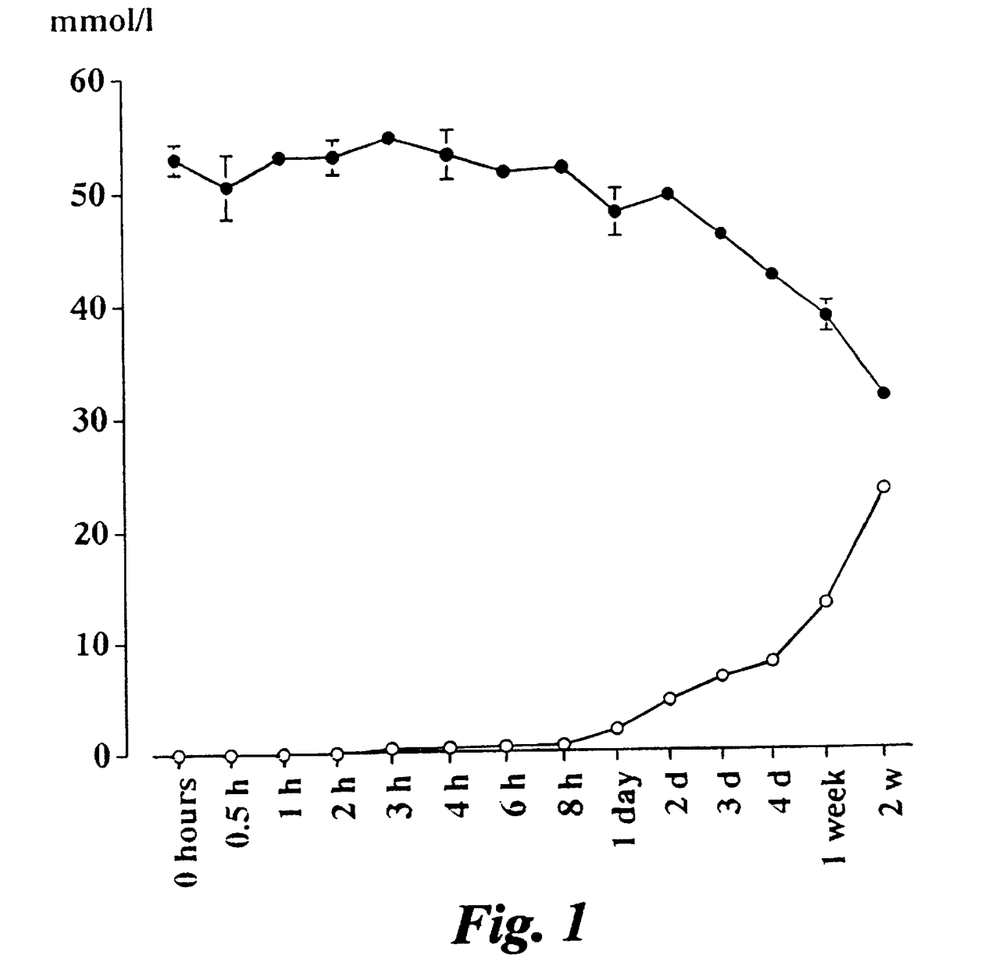
FIGS. 1 and 2 are graphs of creatine concentration against time.
Figure 2:
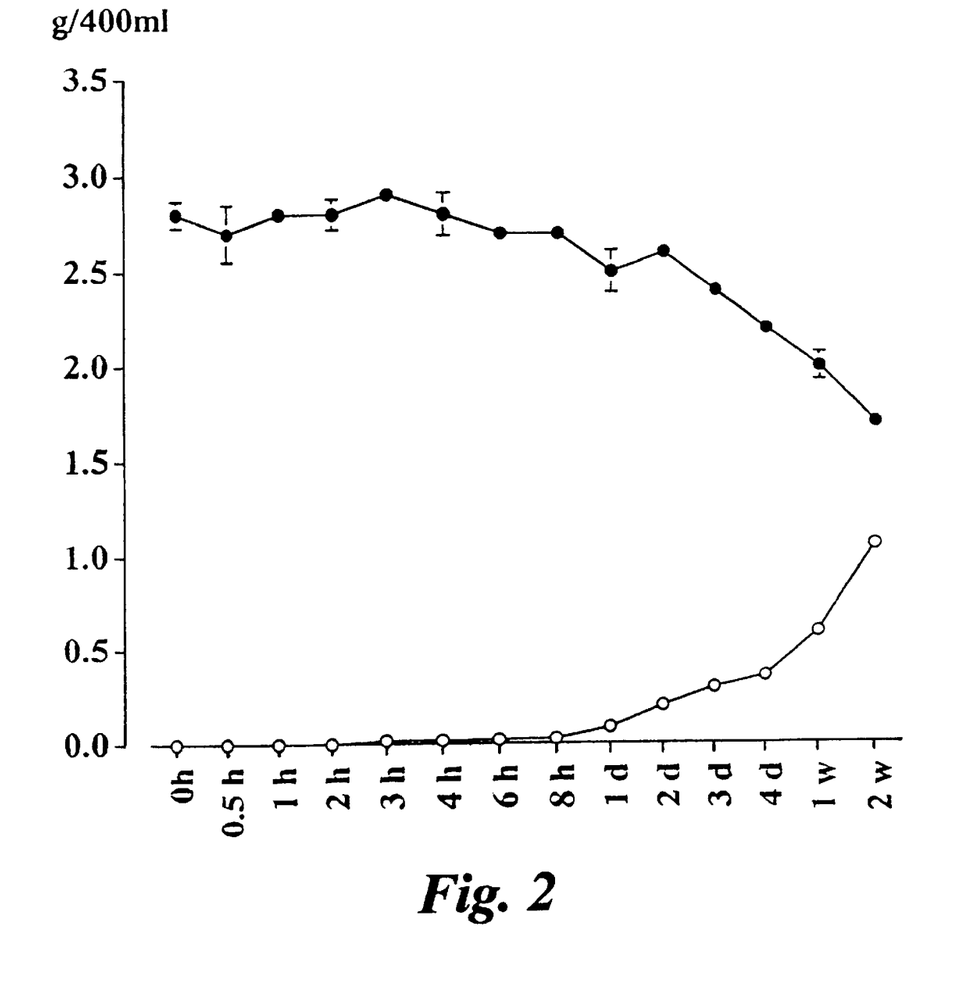
Figure 3:
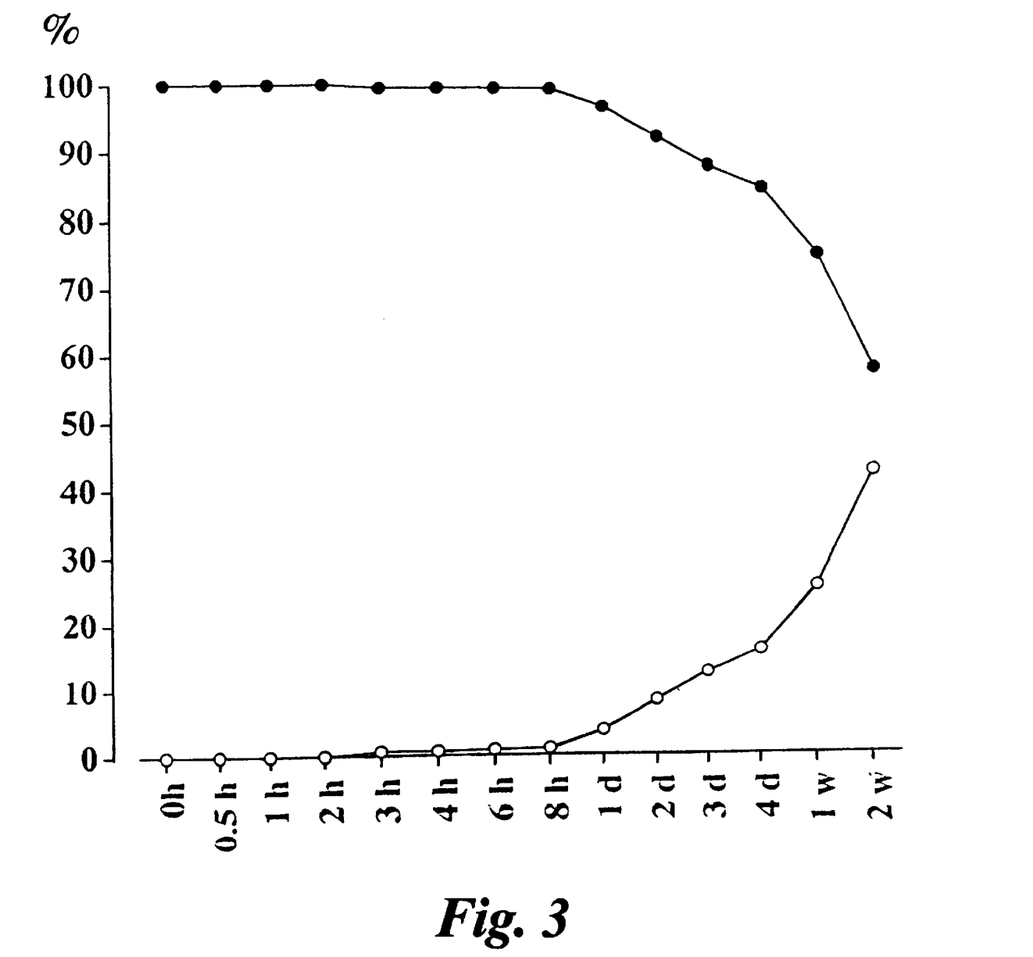
FIGS. 3–6 are graphs of % creatine against time.

These results are also represented graphically in FIGS. 1–3.

FIG. 1 is a graph of mean creatine concentration (filled circles) or creatinine concentration (open circles) in mmol/liter against time (measured in hours, days or weeks)

FIG. 2 is a similar graph showing mean creatine or creatinine composition in grams/400 ml against time.

FIG. 3 is a graph showing percentage creatine unconverted (filled circles) or percentage creatine converted into creatinine (open circles) against time.

From these data it was apparent that acidic solutions of creatine could be stored at ambient temperature for 24 hours with very little loss of creatine. Longer storage (for 2–3 days) was possible without serious loss of creatine).

Example 5

This example relates to a study of the stability of creatine over 3 days in aqueous solutions at different pH values.

42 grams (three×14 gm samples) of the powdered formulation described in the preceding example were dissolved in 750 mls of distilled water warmed to 25° C. seven 100 ml aliquots (termed A–G respectively) were drawn off into polystyrene beakers of known weight and were re-weighed. The pH of the aliquots was adjusted to desired values (A=pH 2.5, B=3.5, C=4.5, D=5.5, E=6.5, F=7.5, G=8.5) using 50% acetic acid or 5N KOH. After pH adjustment the beakers were re-weighed to ensure the increase in volume was less than 5% (i.e. less than 5 mls).

The samples were held at 25° C. for 24 hours, and 5 ml aliquots drawn off for analysis of creatine and creatinine concentration (as described previously) at time points of 0.5 hrs, 4 hrs, 8 hrs, 1 day and 3 days.

The pH of the solutions was also tested, to ensure that the pH did not alter too greatly during the course of the experiment. These results are shown in Table 2 below.

TABLE 2

| | TEST SOLUTION | | | | | | |
|---|---|---|---|---|---|---|---|
| | A | B | C | D | E | F | G |
| Target pH | 2.5 | 3.5 | 4.5 | 5.5 | 6.5 | 7.5 | 8.5 |
| 0.5h pH | — | 3.4 | 5.5 | 5.5 | 6.7 | 7.6 | — |
| 4h pH | — | 3.5 | 4.5 | 5.5 | 6.5 | 7.4 | 8.2 |
| 3d pH | — | 3.7 | 4.7 | 5.5 | 6.6 | 7.3 | 7.6 |

Figure 4:
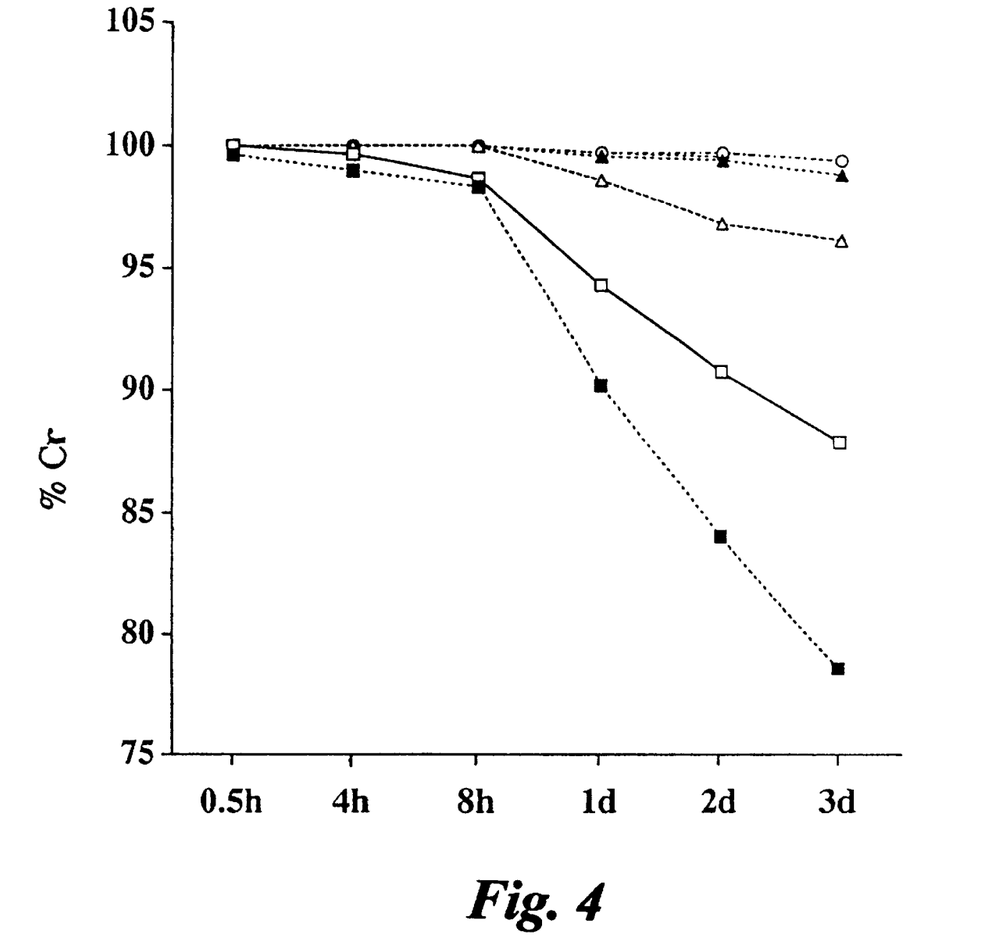

Referring to FIG. 4, the figure shows a graph of % creatine remaining against time (measured in hours or days) for solutions A–F. The results for solutions A (pH 2.5) and G (pH 8.5) are omitted for clarity. The legend is as follows: filled squares=solution B (pH 3.5), open squares-solution C (pH 4.5), open triangles=solution D (pH 5.5), filled triangles=solution E (pH 6.5), and open circles=solution F (pH 7.5).

It can be seen that, in general, the lower the pH the faster the conversion of creatine into creatinine, but even solutions of pH 4.5 or so are reasonably stable for up to 3 days. Breakdown after 3 days at pH 5.5, 4.5 and 3.5 was 4%, 12% and 21% respectively.

In fact it was found that an exception to this general rule was that creatine is more stable at pH 2.5 than at pH 3.5. After 3 days, breakdown at pH 2.5 was found to be ≈13%, similar to that occurring at pH 4.5.

Example 6

This example relates to a study of the stability of creatine over a period of 52 days in aqueous solutons at different pH values held at lower than ambient temperature (specifically, 4° C.).

Firstly, because creatine has poor solubility in water at 4° C., an experiment was performed to ensure that the concentrations of creatine used in the stability determination would not lead to precipitation of creatine over a 5 week period.

The solubility determination was conducted as follows:

1.2 g of creatine monohydrate was dissolved in 100 ml of buffer solutions (prepared by mixing 200 mM $K_2HPO_4$ and 200 mM Acetic acid, and adjusting the pH by the addition of 5M KOH) at pH 3.5, pH 5.0, pH 6.0 and pH 7.0 at room temperature. Dilutions were made with distilled water for each pH value:

A)—no dilution

B)—9:1 (buffer water)

C)—8:2"(buffer water)

D)—7.3"(buffer water)

E)—6.4"(buffer water)

F)—5.5"(buffer water)

Final solutions were stored in capped plastic tubes. The tubes were stored at 4° C., shaken every 2 hours or so and the time of precipitation appearance was noted.

The relative amount of precipitation after 78 hrs storage at 4° C. was noted and the results presented below, in Table 3. Tube D (7:3 dilution) was the highest concentration of creatine which showed no preciptation after 78 hours. The concentration of creatine in tube D was 8.4 gms/liter. Accordingly, the stability determination experiment was performed using the same initial concentration of creatine.

TABLE 3

| Dilution | A | B | C | D | E | F |
|---|---|---|---|---|---|---|
| Initial concentration of creatine monohydrate (g/l) | 12.0 | 10.8 | 9.6 | 8.4 | 7.2 | 6.0 |
| Degree of precipitation by 78 bours | | | | | | |
| pH 3.5 | *** | ** | — | — | — | — |
| pH 5.0 | *** | ** | * | — | — | — |
| pH 6.0 | *** | ** | * | — | — | — |
| pH 7.0 | ** | * | * | — | — | — |

Relative precipitation: * = heavy;  = moderate; * = light; — = none

The stability determination was performed as follows. 14 gms of the formulation described in Example 4 were dissolved in 250 ml of distilled water. Additionally 14 gms of a second formulation were dissolved in 500 mls. The second formulation did not contain any creatine, but was otherwise identical to the formulation described in Example 4. 107 mls of the second solution were added to the first solution, producing a 7:3 dilution.

Four 60 ml aliquots were removed and the pH adjusted with 5M KOH to: A—unadjusted pH; B—pH 5.0; C—pH 6.0; D—pH 7.0. 40 ml aliquots were removed for storage in plastic tubes at 4° C. 0.5 ml samples were removed from A–D and diluted directly into 100 ml distilled water at 0 hours, 2d, 7d, 14d, 28d, 35d and 52d for analysis of creatine and creatinine by HPLC, as described previously. The pH of the samples was also tested to ensure it had not varied over the course of the experiment. The results are shown below.

TABLE 4

| pH of sample over the course of the experiment. | | | | | | | |
|---|---|---|---|---|---|---|---|
| pH values | 0h | 0h | 2d | 7d | 14d | 28d | 35d |
| A | 3.5 | 3.5 | 3.6 | 3.6 | 3.6 | 3.6 | 3.6 |
| B | 5.0 | 5 1 | 5.1 | 5.1 | 5.1 | 5.1 | 5.1 |
| c | 6.0 | 6.1 | 6.1 | 6.1 | 6.1 | 6.1 | 6.1 |
| D | 7.0 | 7.1 | 7.1 | 7.1 | 7.1 | 7.0 | 7.0 |
| Temp (° C.) | 20.0 | 4.0 | 4.0 | 4.0 | 4.0 | 4.0 | 4.0 |

Results of the analysis of the stability of creatine are shown below in Table 5.

TABLE 5

Stability of creatine over 52 days' storage at 4° C.

| | [Cr] or [Cn] in mmol/L Day 0 | | % Cr remaining on day | | | | | |
|---|---|---|---|---|---|---|---|---|
| | [Cr] | [Cn] | 0 | 2 | 7 | 14 | 28 | 35 | 52 |
| A | 60.79 | 0.00 | 100 | 99.4 | 98.6 | 97.0 | 94.0 | 92.7 | 92.1 |
| B | 55.40 | 0.00 | 100 | 100 | 99.4 | 98.8 | 97.0 | 96.0 | 95.8 |
| C | 60.32 | 0.00 | 100 | 100 | 99.7 | 99.7 | 99.3 | 98.6 | 98.6 |
| D | 59.68 | 0.00 | 100 | 100 | 100 | 100 | 99.6 | 99.6 | 99.4 |

Figure 5:
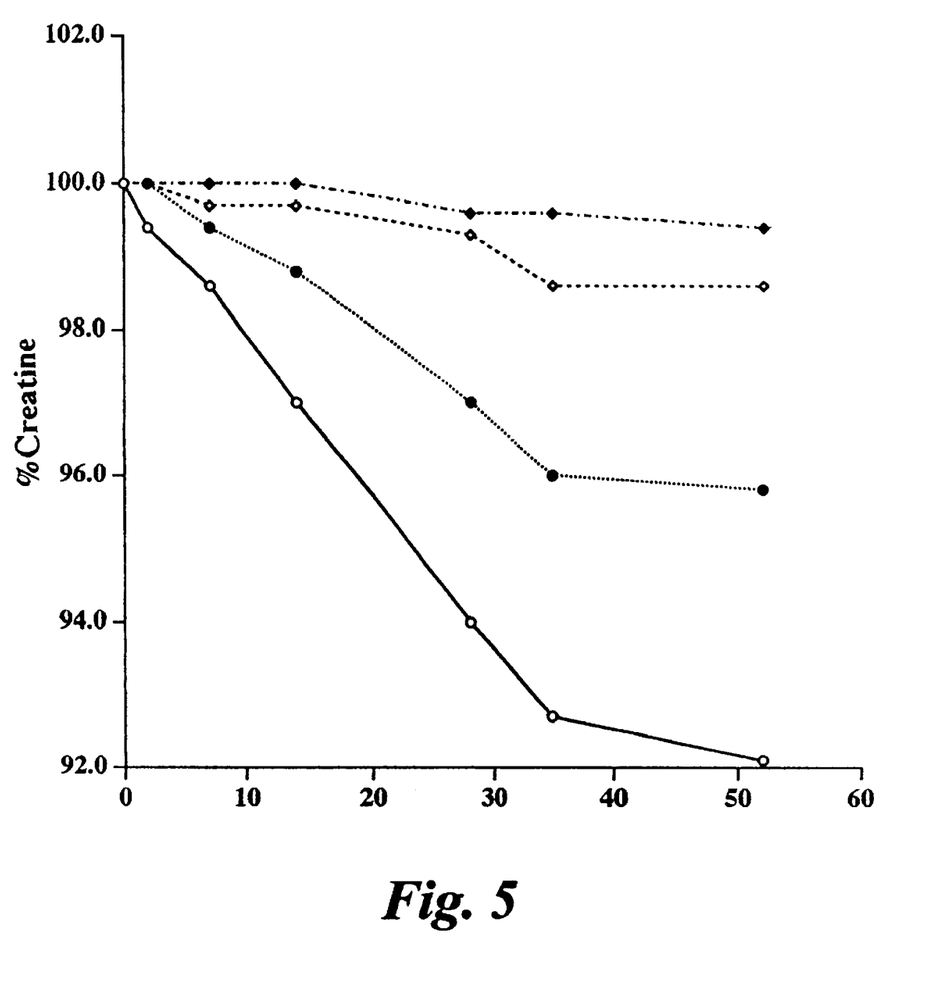

The above results are also represented graphically in FIG. 5. FIG. 5 is a graph of % creatine remaining against time (in days). The open circles with solid line show the results for solution A, the solid circles with dotted line show the results for solution B, the open circles with dashed line show the results for solution C, and the solid circles with dotted and dashed line show the results for solution D. These data demonstrate that even at a pH as low as 3.5–3.6, after 5 weeks' storage 4° C. only 7.3% of the creatine had been converted to creatinine, and very little further change had occurred by day 52, indicating that an equilibrium had been attained leaving significant amounts of creatine available for physiological benefit. Thus an acidic formulation comprising creatine can be prepared and stored successfully especially with storage at temperatures lower than ambient.

Example 7

This examples relates to a study of the stability of creatine over several weeks in different (acidic) commercially available yogurts, during storage at 4° C. The study was performed as follows.

Figure 6:
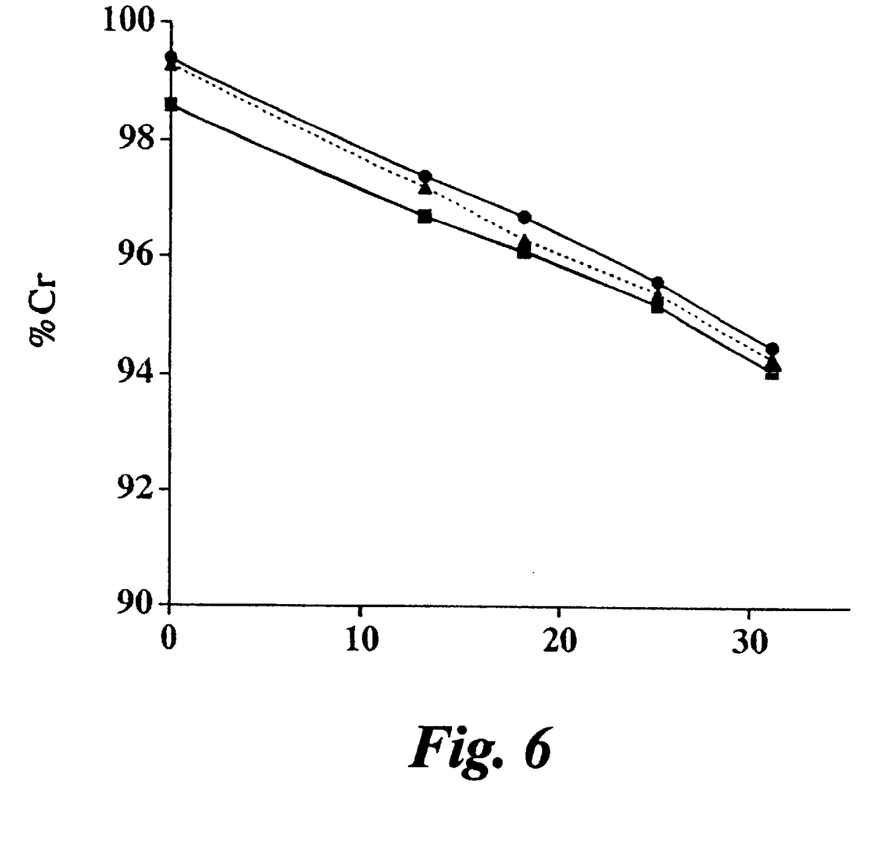

0.5 gms of creatine monohydrate was mixed with 100 gms of a commercially available yogurt to give a creatine concentration of about 3.4 mmol per 100 gms. The supplemented yogurt was placed in a domestic refrigerator set at 4° C. At various times, 2 gms of the supplemented yogurt was taken up into 100 mls of distilled water. 1 ml of the resulting solution was filtered using a Whatman microfilter of pore size 12 kilodaltons, and the clear filtrate was assayed for creatine and creatinine concentrations as described previously. Three different types of yogurt (purchased from Tesco's stores) were used in the experiment: a low fat natural yogurt, a "healthy eating bio" yogurt, and a Fage Greek yogurt. The results of the creatine analysis are shown below in Table 6, and are represented graphically in FIG. 6. FIG. 6 shows a graph of % creatine remaining against time (in days). The squares show the results for the low fat yogurt, the circles show the results for the "healthy eating" yogurt, and the triangles show the results for the Greek yogurt.

The stability of creatine in the different yogurts was extemely similar. The amount of conversion of creatine to creatinine was about 6% or less after 31 days' storage at 4° C. The presence of live bacteria in the yogurt does not appear to have any detrimental effect.

Thus yogurt represents an extremely useful vehicle for a creatine-containing composition, especially as yogurts are conventionally handled and stored at lower than ambient temperatures—the presence of creatine in the yogurt does not necessitate any additional handling requirements in relation to temperature of storage.

TABLE 6

Stability of creatine in three different commercially available yogurts

| | Low fat natural yogurt | Healthy eating bio yogurt | Greek yogurt |
|---|---|---|---|
| Starting pH | 388 | 4.21 | 4.11 |
| Day | % creatine | % creatine | % creatine |
| 0 | 98.6 | 99.4 | 99.3 |
| 13 | 96.7 | 97.4 | 97.2 |
| 18 | 96.1 | 96.7 | 96.3 |
| 25 | 95.2 | 95.6 | 95.4 |
| 31 | 94.1 | 94.5 | 94.3 |

We claim:

1. An acidic yogurt or similar semi-liquid foodstuff composition for human consumption, said composition being unflavored or fruit flavored, comprising creatine, said creatine being substantially stable at ambient temperature or below.

2. A composition according to claim 1, comprising a fruit-flavoring.

3. A composition according to claim 1, having a pH in the range 2.5–6.5

4. A composition according to claim 1, having a pH in the range 3.0–6.0.

5. A composition according to claim 1, comprising pyruvate and/or dihydroxyacetone.

6. A composition according to claim 1, comprising pyruvate as the sodium, potassium, calcium or magnesium salts thereof.

7. A composition according to claim 1, comprising one or more additional components selected from the group consisting of: vitamins, lipids, carbohydrates, amino acids, trace elements, colourings, flavors, artificial sweeteners, anti-oxidants, stabilisers, preservatives, and buffers.

8. A composition according to claim 1, provided as unitary doses.

9. A stable, dry powder composition comprising creatine, said composition being unflavored or fruit flavored, which, when mixed with water or an aqueous solution, provides an acidic drink for human consumption, said creatine being substantially stable at ambient temperature or below.

10. A composition according to claim 9, wherein the composition provides a drink which is isotonic and/or comprises electrolytes.

11. A composition according to claim 9, wherein the composition provides an isotonic drink comprising electrolytes.

12. A composition according to claim 9, wherein the composition when dissolved in water provides a drink having a pH in the range 2.5–6.5.

13. A composition according to claim 12, providing a drink having a pH in the range 3.0–6.0.

14. A composition according to claim 9, comprising pyruvate and/or dihydroxyacetone.

15. A composition according to claim 9, comprising pyruvate as the sodium, potassium, calcium or magnesium salts thereof.

16. A composition according to claim 9, comprising one or more additional components selected from the group consisting of vitamins, lipids, carbohydrates, amino acids, trace elements, colourings, flavors, artificial sweeteners, anti-oxidants, stabilisers, preservatives, and buffers.

17. A composition according to claim 9, provided as unitary doses.

18. A composition according to claim 17, wherein each dose contains a physiologically effective quantity (of the order of 3 gms) of creatine.

19. A method of supplying an acidic creatine-containing yogurt or similar semi-liquid foodstuff for human consumption, the method comprising the steps of: obtaining a creatine-containing substance; and mixing the creatine-containing substances with a yogurt or similar semi-liquid foodstuff.

20. A method of providing a creatine-containing acidic composition as a dry, stable powder which, when mixed with water or an aqueous solution gives an acidic fruit-flavored drink comprising creatine, the method comprising the steps of: providing a creatine-composition; drying the composition; and packaging the dried composition.

21. A method according to claim 3, wherein the dried composition is packaged in unitary doses.

* * * * *